(12) United States Patent
Park

(10) Patent No.: US 7,136,705 B1
(45) Date of Patent: Nov. 14, 2006

(54) METHOD AND APPARATUS FOR MONITORING SENSOR PERFORMANCE DURING RATE-RESPONSIVE CARDIAC STIMULATION

(75) Inventor: Euljoon Park, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 783 days.

(21) Appl. No.: 10/160,766

(22) Filed: May 31, 2002

(51) Int. Cl.
  *A61N 1/18* (2006.01)
(52) U.S. Cl. .......................... 607/27; 607/18; 607/19; 607/20; 607/21; 607/22; 607/23
(58) Field of Classification Search ............ 607/9, 607/27, 18–24; 600/300; 702/185
See application file for complete search history.

(56) References Cited

U.S. PATENT DOCUMENTS

| 4,702,253 A | 10/1987 | Nappholz et al. | 128/419 |
|---|---|---|---|
| 4,901,725 A | 2/1990 | Nappholz et al. | 128/419 |
| 4,940,053 A | 7/1990 | Mann et al. | 128/419 |
| 5,097,831 A | 3/1992 | Lekholm | 128/419 |
| 5,387,229 A | 2/1995 | Poore | 607/18 |
| 5,423,867 A | 6/1995 | Poore et al. | 607/17 |
| 5,425,750 A | 6/1995 | Moberg | 607/19 |
| 5,476,483 A | 12/1995 | Bornzin et al. | 607/17 |
| 5,562,711 A | 10/1996 | Yerich et al. | 607/17 |
| 5,620,471 A * | 4/1997 | Duncan | 607/14 |
| 5,626,622 A | 5/1997 | Cooper | 607/18 |
| 5,720,769 A | 2/1998 | Van Oort et al. | 607/17 |
| 5,836,988 A | 11/1998 | Cooper et al. | 607/19 |
| 6,275,733 B1 | 8/2001 | Park et al. | 607/18 |

* cited by examiner

*Primary Examiner*—Mark Bockelman

(57) ABSTRACT

A cardiac stimulation device and method monitor and store discrepancies in sensor indicated rates determined from two or more sensors generating signals related to metabolic demand. One feature included in the present invention is a sensor cross-check record that stores the time, duration and sensor indicated rates whenever individual sensor indicated rates differ by more than a discrepancy threshold. This record allows a clinician to monitor an abnormal patient condition or determine if a sensor is not functioning properly or is programmed sub-optimally. Another feature provided by the present invention is a sensor cross-check histogram in which sensor indicated rate differences are stored. Histogram data aids the clinician in selecting programmable operating parameters that control the calculation of sensor indicated rates and the rate response of the cardiac stimulation device.

34 Claims, 8 Drawing Sheets

METHOD AND APPARATUS FOR MONITORING SENSOR PERFORMANCE DURING RATE-RESPONSIVE CARDIAC STIMULATION

FIELD OF THE INVENTION

The present invention relates generally to an implantable cardiac stimulation device capable of providing rate-responsive stimulation according to multiple sensor signals and, in particular, to a method for monitoring discrepancies that occur between individual sensor indicated rates.

BACKGROUND OF THE INVENTION

In the normal human heart, the sinus node, generally located near the junction of the superior vena cava and the right atrium, constitutes the primary natural pacemaker initiating rhythmic electrical excitation of the cardiac chambers. The cardiac impulse arising from the sinus node is transmitted to the two atrial chambers, causing a depolarization known as a P-wave and the resulting atrial chamber contractions. The excitation pulse is further transmitted to and through the ventricles, via the atrioventricular (A-V) node and a ventricular conduction system, causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate.

A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

Early pacemakers delivered stimulation pulses to the heart at a fixed rate. Fixed rate pacing, however, is not physiological in that periods of increased activity or metabolic demand are not accompanied by the normal physiological rise in heart rate. Rate-responsive pacemakers were, therefore, introduced. Rate-responsive pacemakers employ sensors that indicate changes in physical activity or metabolic demand.

One commonly used sensor is an accelerometer that is positioned within the housing of the stimulation device that is implanted within the patient's body. As the patient becomes more active, the accelerometer measures the resulting acceleration and provides an activity signal that is indicative of the increased acceleration experienced by the patient.

Activity sensors of this type are generally thought to provide a good indication of the metabolic demand of the patient for newly initiated, brisk, low-level activity. In other words, when the patient initiates a new brisk, low-level activity, such as walking and the like, the accelerometer in the activity sensor provides a good indication of the sudden increase in the level of activity of the patient which generally results in heightened metabolic demand requiring the heart to deliver more oxygenated blood.

While activity sensors of this type are adequate for providing an indication of the onset of brisk, low-level activity, these sensors have several shortcomings. For example, the signal that is often provided by such activity sensors becomes blunted when the patient is engaged in high exertion exercise. In other words, when the patient is heavily engaged in a particular physical activity, the activity signal may not provide a sufficient indication to the control unit of the need for more oxygenated blood as a result of the increased activity. As an illustration, the output signal from a typical activity signal can be inaccurate for assessing the patient's actual metabolic need when the patient is performing an action like carrying a heavy object.

The degree of acceleration detected by the activity sensor is likely to correspond to a perceived low metabolic demand activity, such as walking, and would not account for the increase in metabolic demand as a result of carrying the heavy object. Moreover, acceleration-based activity sensors are also subject to providing false readings as a result of the patient experiencing accelerations that are unrelated to physical activity, such as, for example, the patient traveling on a bumpy road in a vehicle.

Other types of physiologic sensors may be used to provide an indication of metabolic demand. One common type of physiologic sensor is a minute ventilation sensor that measures the respiration rate and tidal volume of the patient's respiration. Respiration is normally related to metabolic demand. Therefore, the rate at which a patient is breathing and the volume of air being breathed is normally indicative of the metabolic demand of the patient.

One typical way of obtaining a minute ventilation signal is to periodically measure the transthoracic impedance between a lead implanted within the patient's heart and an indifferent electrode, such as the housing of the implanted stimulation device. As the transthoracic impedance is proportional to the chest volume, measuring this particular impedance value provides an indication as to the degree to which the patient's chest is expanding and contracting and the rate at which such expansion and contraction is occurring. The greater the patient's breathing rate and the greater the tidal volume of the breaths, the more likely it is that the patient has a heightened need for delivery of oxygenated blood by the heart.

While physiologic sensors, such as minute ventilation sensors, provide a strong indication of the metabolic demand of the patient, these sensors also have several disadvantages for use in determining the needed cardiac stimulation rate. In particular, the values provided by these sensors often lag in time behind the actual metabolic demand of the patient. Consequently, these sensors are typically not particularly well suited for providing the sole indication of the actual metabolic demand of the patient when the patient is initiating or ceasing physical exertion.

To address the problems associated with both of these types of sensors, rate responsive pacing systems have been developed which utilize the signals from two or more types of sensors to determine a desired heart stimulation rate.

One goal of dual or multi-sensor rate response devices is to provide the most normal sinus response to changes in activity and metabolic demand possible by determining the rate response based on two or more sensor indicated rates. Differences in sensor indicated rates do exist due to different response times of the sensors or different sensitivities to a particular form of activity or exertion. Therefore, algorithms for determining a stimulation rate adjustment based on two or more sensors may include assigning various weighting factors to received sensor signals or applying different processing parameters to sensor signals (e.g., filtering).

Differences between sensor indicated rates (or sensor levels) provided by multiple sensors may also arise when an abnormal patient condition exists. For example, Cheyne-Stokes respiration, which is the waxing and waning of breathing, is known to occur and gradually worsen in heart failure patients. During Cheyne-Stokes respiration, a minute ventilation sensor will sense a high minute ventilation, even during rest, followed by a period of very low minute ventilation. The high minute ventilation during an episode of Cheyne-Stokes respiration would falsely indicate a high metabolic need and therefore an unnecessarily high sensor indicated rate. Thus, a minute ventilation sensor may be reflecting periods when respiration is abnormal rather than when an actual change in metabolic demand occurs.

A discrepancy between individual sensor indicated rates (or sensor levels) may arise when one sensor is functioning abnormally, e.g., responding to extraneous noise, or when the sensor indicated rate calculations are programmed to be either too sensitive or too insensitive to sensor signal changes. When programmed optimally, the sensor indicated rate used to adjust stimulation rate will be determined from each sensor some of the time.

If the rate is adjusted in response to one sensor, all or a majority of the time, the benefit of dual or multi-sensor rate determination may be lost. One sensor may be programmed such that the sensor indicated rate is too sensitive to sensor signal changes, or another sensor may be programmed such that the sensor indicated rate is not sensitive enough to sensor signal changes.

It would be desirable to provide a cardiac stimulation system and method for monitoring sensor indicated rate discrepancies such that the frequency and probable cause of such discrepancies can be understood. Such monitoring would allow abnormal patient conditions to be tracked or adjustments to operating parameters controlling the rate response based on sensor indicated rates to be optimized.

To this end, a method is needed for detecting discrepancies in sensor indicated rates and recording the occurrence of such discrepancies. It is also desirable, in a dual or multi-sensor, rate-responsive stimulation device, to provide a method for documenting sensor indicated rate differences so that the programming of operating parameters used in calculating sensor indicated rates can be optimized.

SUMMARY

The present invention addresses these needs by providing an implantable cardiac stimulation device capable of monitoring and storing discrepancies in sensor indicated rates determined from two or more sensors generating signals related to metabolic demand. One feature included in the present invention is a sensor cross-check record that stores the time, duration, and sensor indicated rates whenever individual sensor indicated rates differ by more than a discrepancy threshold. This record allows a clinician to monitor an abnormal patient condition, and to determine if a sensor is not functioning properly or is programmed sub-optimally.

Another feature of the present invention is a sensor cross-check histogram in which sensor indicated rate differences are stored. Histogram data aids the clinician in selecting programmable operating parameters that control the calculation of sensor indicated rates and the rate response of the cardiac stimulation device.

The foregoing and other features of the present invention are realized by providing an implantable cardiac stimulation device equipped with data acquisition capabilities and two or more sensors that provide a signal related to metabolic demand. In a preferred embodiment, the stimulation device includes a control system for controlling the operation of the device and for receiving sensor signals and calculating a signal indicated rate based on these received signals. The control system controls the rate of stimulation pulse delivery to the heart and is able to adjust the stimulation rate according the calculated sensor indicated rates so that the metabolic needs of the patient are met.

The stimulation device further includes a set of leads for receiving cardiac signals and for delivering atrial and ventricular stimulation pulses; a set of sensing circuits comprised of sense amplifiers for sensing and amplifying the cardiac signals; a sampler, such as an A/D converter for sampling cardiac signals; and pulse generators for generating atrial and ventricular stimulation pulses.

In addition, the stimulation device includes memory for storing data acquired during monitoring functions and operational parameters for the control system, such as stimulation parameter settings and timing intervals. The device also includes a telemetry circuit for communicating with an external device so that operational parameters may be non-invasively programmed and stored data may be downloaded and displayed.

When operating according to a preferred embodiment, a record of discrepancies between individual sensor indicated rates is stored in a sensor cross-check record in the device memory for later downloading and display. A threshold difference between individual sensor indicated rates is pre-defined and can be a user-programmed value or a calculated value relative to the base stimulation rate and the maximum allowed sensor rate.

Whenever the difference between individual sensor indicated rates exceeds the threshold difference, referred to as the "discrepancy threshold," the time and duration of the discrepancy and the individual sensor indicated rates are stored in the device memory. Data may be stored in a circular memory such that a given number of the most recent discrepancy events are stored. The data stored in the sensor cross-check record may be downloaded to an external device and displayed for analysis by a clinician.

In one embodiment, the discrepancy of sensor indicated rates, the time at which the discrepancy occurred, and the duration of the discrepancy may also be used by the stimulation device to determine the appropriate stimulation rate response taken by the control system. Based on the discrepancy data, the stimulation rate may not be adjusted at all or the stimulation rate may be adjusted according to one sensor indicated rate determined to be the most reliable indicator of the patient's metabolic need at that time.

The sensor cross-check record may operate independently or in combination with a sensor cross-check histogram, which documents the frequency of differences in individual sensor indicated rates. The sensor cross-check histogram operates by first assigning a set of histogram bins to each sensor. Each bin within a set of histogram bins is assigned to a rate difference. Whenever a difference in individual sensor indicated rates is detected, the value stored in the histogram bin assigned to the sensor indicating the greatest rate and corresponding to the detected rate difference is increased by one.

The histogram data may be downloaded to an external device and displayed for analysis by a clinician. If the frequency of sensor indicated rate differences is evenly distributed between the sensors and approximates a normal distribution around a difference of zero, the sensors are most likely functioning properly and programmed sufficiently.

However, if one sensor is frequently indicating a greater rate than the other sensor, the parameters controlling the sensor-indicated rate determinations are probably not programmed in an optimal fashion. The histogram information aids the clinician in programming the operating parameters more appropriately. Other abnormalities, such as an abnormal patient condition or malfunction of a sensor, may also be identified by observing a histogram of the sensor-indicated rate differences.

The present invention thus provides a device and method for monitoring the discrepancies that occur between sensor indicated rates in dual or multi-sensor rate responsive cardiac stimulation devices. Such monitoring will aid clinicians and researchers in understanding why and when deviations in sensor behavior occur. Such monitoring further allows abnormal patient conditions to be tracked, and the programming of the rate response to sensor signals to be optimized, either automatically or manually.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at monitoring discrepancies between individual sensor indicated rates (or sensor levels) in a dual or multi-sensor rate responsive cardiac stimulation device. A cardiac stimulation device possessing rate responsive capabilities will thus be described in conjunction with FIGS. 1 and 2, in which the features of the present invention could be implemented. It is recognized, however, that numerous variations of such a device exist in which the methods of the present invention could be implemented without deviating from the scope of the present invention.

Figure 1:
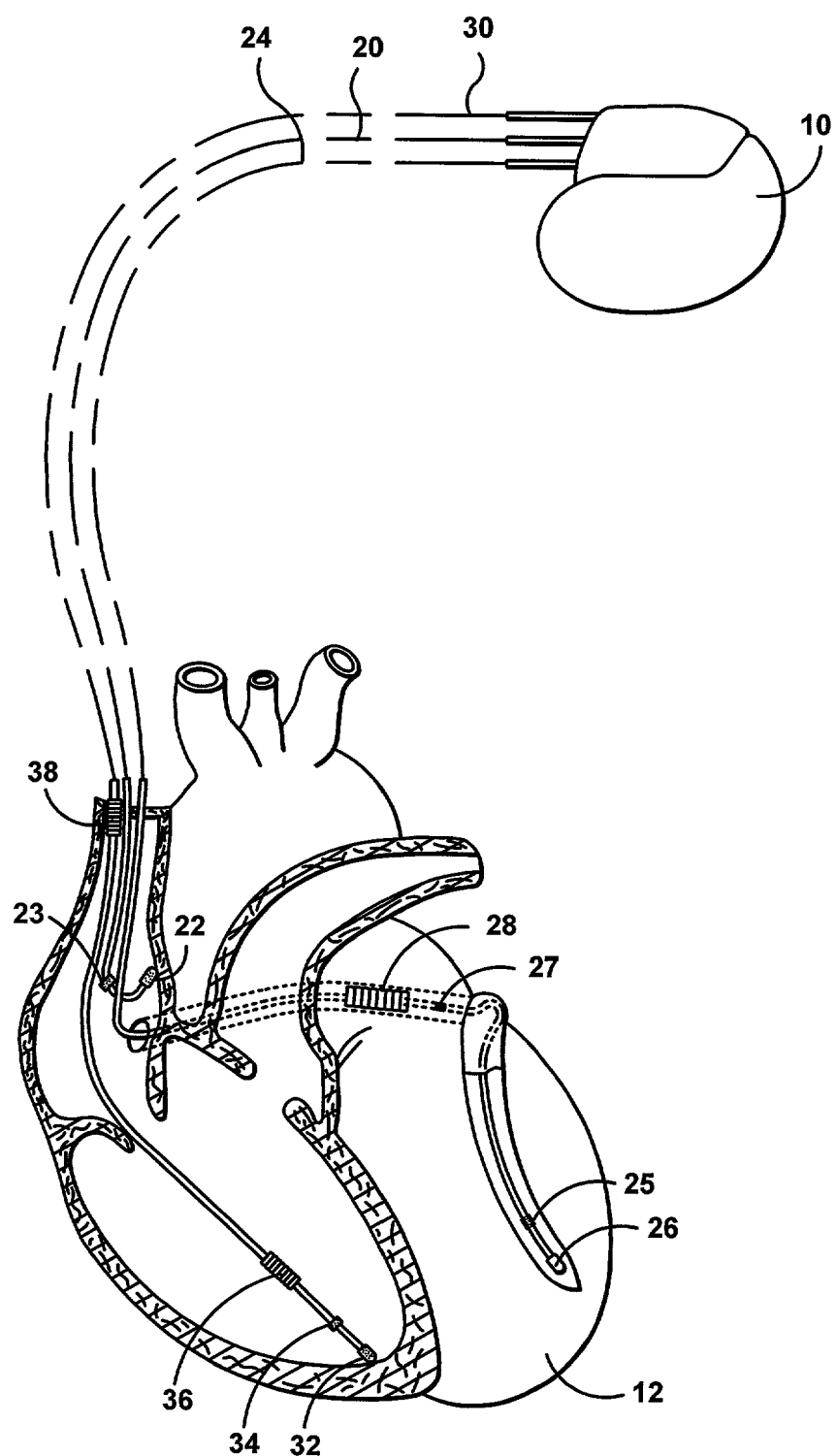
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using: at least a left ventricular tip electrode 26 for unipolar configurations or in combination with left ventricular ring electrode 25 for bipolar configurations; left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
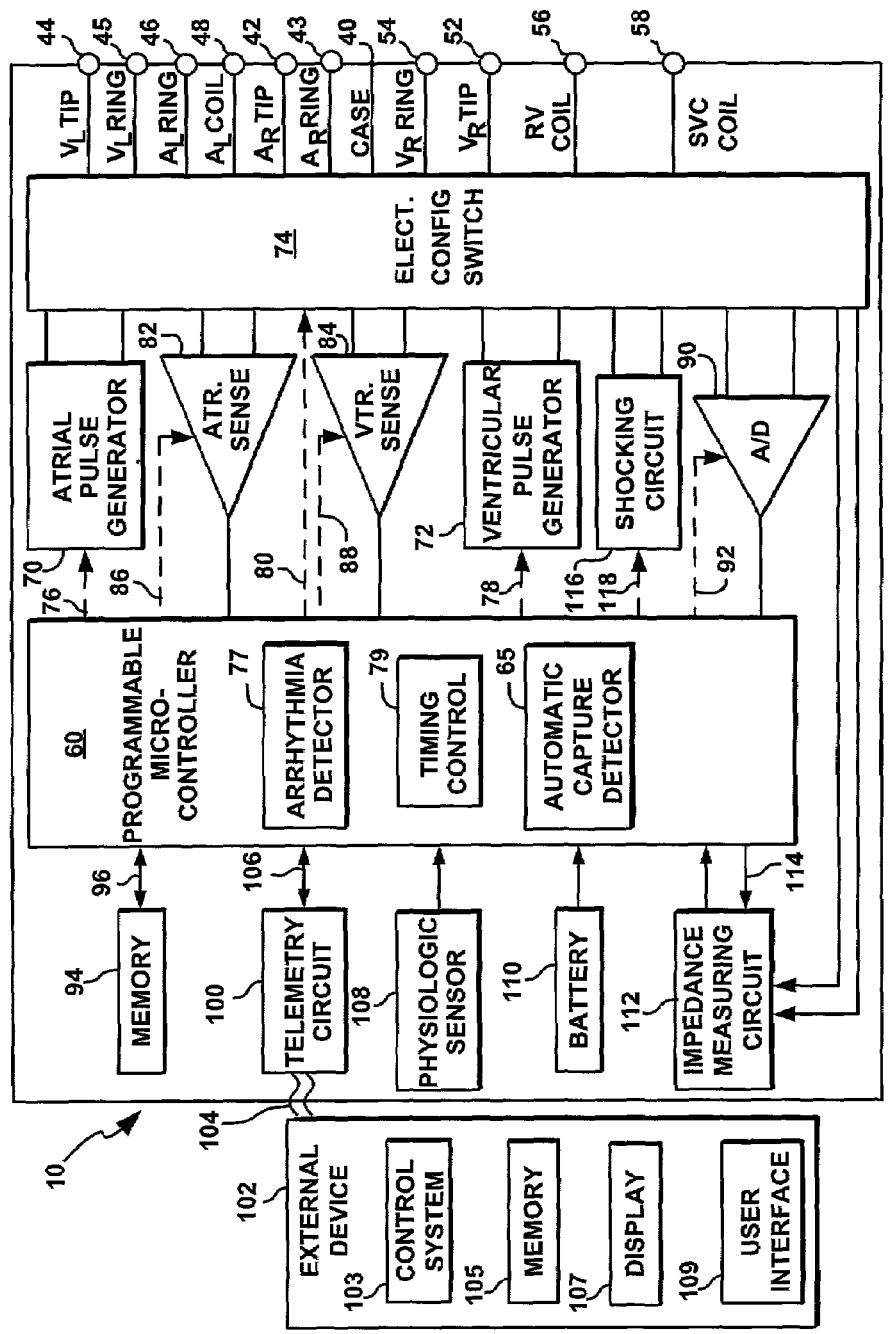
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can," "case," or "case electrode," and which may be programmably selected to act as the return electrode for all "unipolar" modes. The housing 40 may further be used as a return electrode alone or in combination with one or more of the coil electrodes 28, 36, or 38, for defibrillation shocking purposes. The stimulation device 10 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector may also include a right atrial ring terminal ($A_R$ RING) 43 for connection to the right atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.), as well as to keep track of the timing of refractory periods, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation. The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" refers to the process of noting an electrical signal. "Detection" refers to the step of confirming that the sensed electrical signal as the signal being sought by the detector. As an example, "detection" applies to the detection of both proper rhythms (i.e., "R wave" or "R wave") as well as improper disrhythmias including arrhythmia and bradycardia (e.g., detection of the absence of a proper rhythm).

The timing intervals between sensed events (e.g., P-waves, R-waves, and depolarization signals associated with fibrillation which are sometimes referred to as "F-waves" or "Fib-waves") are then classified by the arrhythmia detector 77 by comparing them to a predefined rate zone limit (e.g., bradycardia, normal, low rate ventricular tachycardia, high rate ventricular tachycardia, and fibrillation rate zones) and various other characteristics (e.g., sudden onset, stability, physiologic sensors, and morphology, etc.), in order to determine the type of remedial therapy that is needed (e.g., bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture." In the embodiment shown in FIG. 2, the microcontroller 60 includes an automatic capture detector 65 that searches for an evoked response signal following a stimulation pulse during a "detection window" set by timing control circuitry 79. The microcontroller 60 enables the data acquisition system 90 via control signal 92 to sample the cardiac signal that falls in the capture detection window. The sampled signal is evaluated by automatic capture detector 65 to determine if it is an evoked response signal based on its amplitude, peak slope, morphology or another signal feature or combination of features. The detection of an evoked response during the detection window indicates that capture has occurred.

Capture detection may occur on a beat-by-beat basis or on a sampled basis. When loss of capture is detected, a safety, back-up pulse is delivered shortly after the primary pulse in order to prevent asystole. Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high output level or the level at which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, depicted in FIG. 2 as an external programmer but could also be a transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

External device 102 is shown, in this embodiment, to include a control system 103 for controlling the programming and testing the operation of the external device 102; a memory 105 for storing operational parameters or other data downloaded from stimulation device 10; a display 107 for displaying downloaded data or results of issued programming commands; and a user interface 109 for entering programming commands or requests to retrieve data stored in stimulation device 10.

The stimulation device 10 may further include a physiologic sensor 108, commonly referred to as a "rate-responsive" sensor because it is typically used to adjust stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

While the physiologic sensor 108 is shown as being contained within the stimulation device 10, it is to be understood that the physiologic sensor 108 may alternatively be external to the stimulation device 10, yet still be implanted within, or carried by the patient. Preferably, physiologic sensor 108 includes two or more sensors for detecting multiple signals related to the metabolic need of the patient. A common type of rate responsive sensor is an activity sensor, such as an accelerometer or a piezoelectric crystal, which is mounted within the housing 40 of the stimulation device 10.

Other types of physiologic sensors are also known, for example, sensors that sense the oxygen content of blood, respiration rate and/or minute ventilation, pressure, electrogram-based signals, pH of blood, temperature of blood etc. Any sensor may be used which is capable of sensing a physiological parameter that corresponds to the metabolic demand of the patient.

In one embodiment of the present invention, an activity sensor and a minute ventilation sensor are combined in physiologic sensor 108 to provide two signals for determining an appropriate rate response.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 μA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation;

measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

If it is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
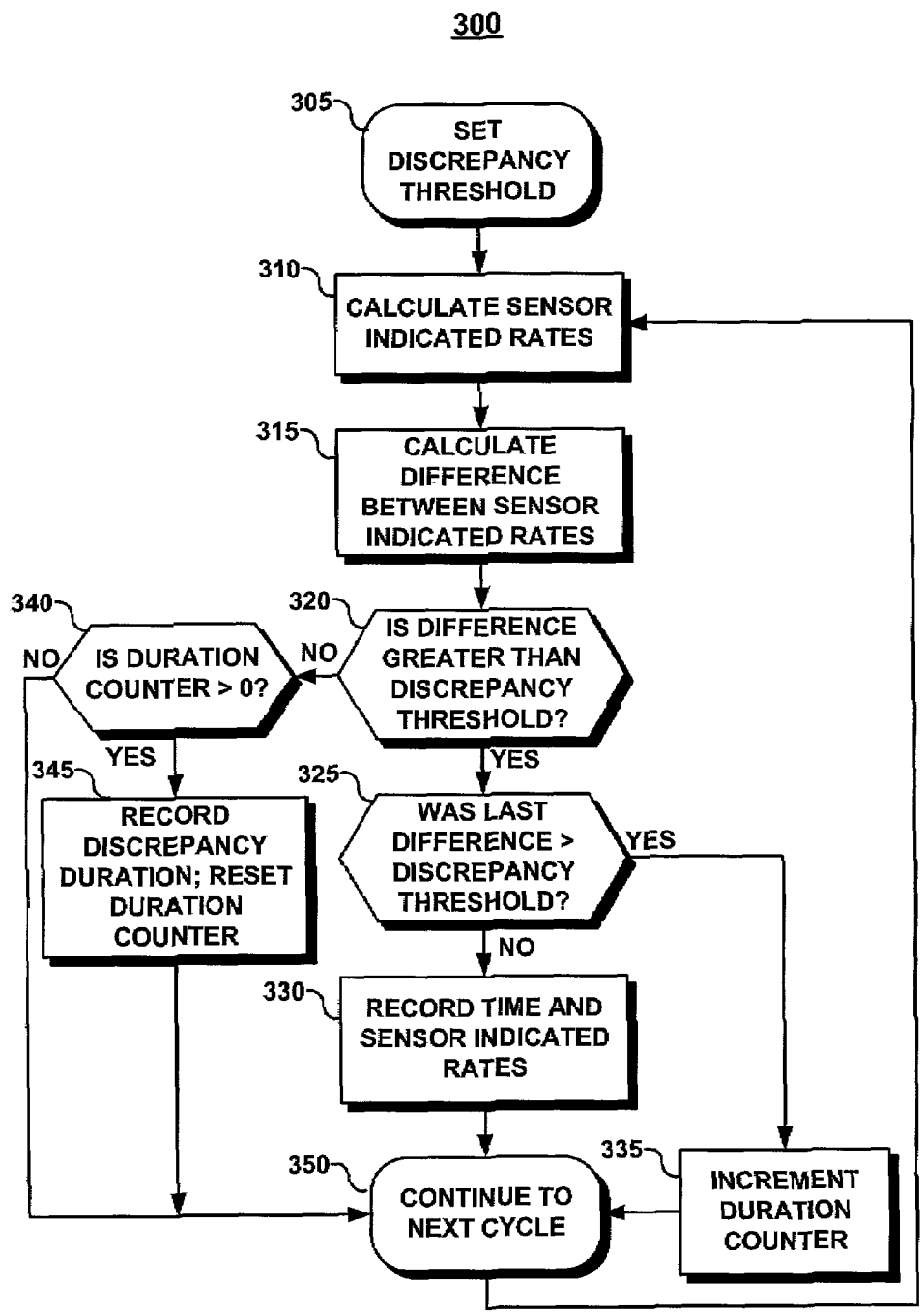
FIG. 3 is a flow chart that illustrates a method implemented by the stimulation device of FIGS. 1 and 2, for recording incidents of sensor indicated rate discrepancies.

In FIG. 3, a flow chart is shown describing an overview of the operation and novel features implemented in one embodiment of the device 10 for monitoring discrepancies between individual sensor indicated rates when multiple sensors of metabolic need are used to determine a rate response. In this flow chart, and the other flow charts described herein, the various algorithmic steps are summarized in individual "blocks." Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The method 300 shown in FIG. 3 represents a sensor cross check record feature provided by the present invention and implemented by the device 10. The sensor-cross check record provides a record of discrepancies between individual sensor indicated rates in dual or multi-sensor rate responsive stimulation devices. A record of sensor indicated rate discrepancies allows the cause and frequency of such discrepancies, for example an abnormal patient condition or abnormal sensor function, to be determined such that the rate response behavior of the stimulation device 10 can be optimized.

Figure 4:
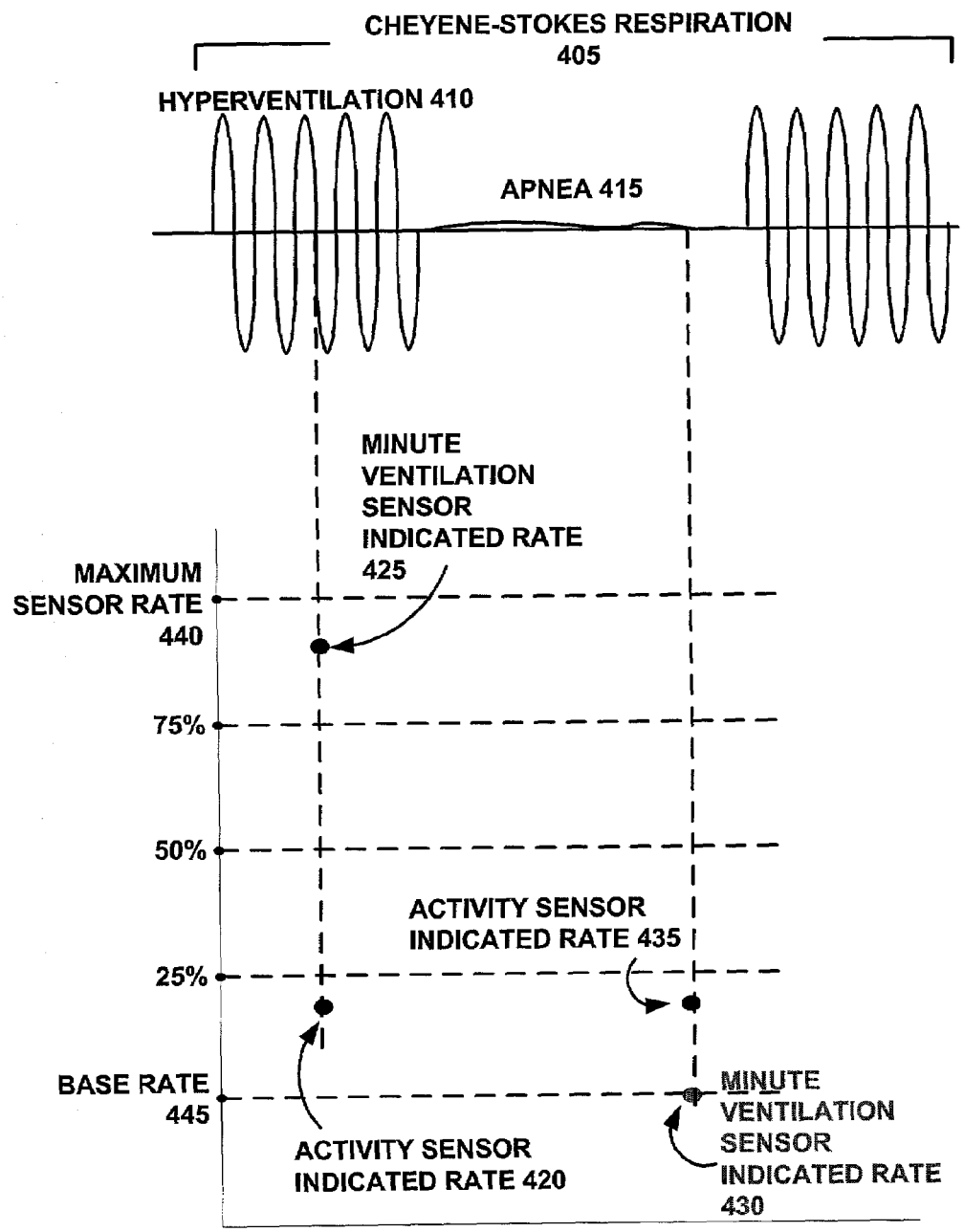
FIG. 4 is an illustration of the breathing pattern during Cheyne-Stokes respiration and the corresponding sensor indicated rate discrepancy that could occur between a minute ventilation sensor and an activity sensor.

As an illustration, FIG. 4 depicts an abnormal patient condition known as Cheyne-Stokes respiration 405, characterized by the periodic waxing and waning of respiration rate and depth, which is commonly observed among heart failure patients. A cyclical period of hyperventilation 410, characterized by rapid, deep breaths, is followed by a period of shallow breathing or even apnea 415 over a cycle of approximately 1 to 3 minutes.

In device 10, when an activity sensor is combined with a minute ventilation sensor, the sensor indicated rate determined from the minute ventilation sensor during these periods of Cheyne-Stokes respiration will differ greatly from the sensor indicated rate determined from the activity sensor. This type of discrepancy in sensor indicated rates is illustrated in FIG. 4 where the minute ventilation indicated rate 425 determined during hyperventilation is high, and an activity sensor indicated rate 420 is low.

The patient may be in a continuous state of low level activity as appropriately indicated by the activity sensor but the minute ventilation sensor falsely indicates a high metabolic need. If sensor indicated rates are determined during the apneic period following the hyperventilation, a low metabolic demand is indicated by the minute ventilation sensor indicated rate 430, while the activity sensor indicated rate 435 continues to indicate the same low level of activity. In a preferred embodiment, the sensor indicated rates are determined on a beat-to-beat basis.

The sensor cross check record provided by the present invention allows for discrepancies in sensor indicated rates, such as that illustrated in FIG. 4, to be documented so that a clinical analysis may be made as to reason and frequency of occurrence of such discrepancies.

The method 300 shown in FIG. 3 for performing a sensor cross check record is initiated at step 305 where a discrepancy threshold is set. A discrepancy threshold is defined as the minimum difference between two sensor indicated rates that must exist in order to trigger the recording of a discrepancy incident. The discrepancy threshold may be a programmed setting. It may also be a calculated value based, for example, on the programmed base rate and the programmed maximum sensor rate.

A base rate refers to a stimulation rate that is appropriate for maintaining the metabolic needs of the patient when he or she is alert but relatively inactive, for example 65 beats per minute. The maximum sensor rate is the maximum stimulation rate to be delivered by device 10 during periods of high metabolic demand. Preferably, the discrepancy threshold is on the order of half the difference between the maximum sensor rate and the base rate, as expressed by the following equation (1):

$$\text{Discrepancy Threshold} = 0.5 \times (\text{maximum sensor rate} - \text{base rate}) \quad (1)$$

At step 310, the microcontroller 60 calculates the sensor indicated rates from the signals received from each sensor included in physiologic sensor 108. At step 315, the difference between the sensor indicated rates are calculated and compared to the discrepancy threshold at decision step 320.

In the example of FIG. 4, the difference between the minute ventilation sensor indicated rate 425 and the activity sensor indicated rate 420 determined during the period of hyperventilation is greater than half the difference between the maximum sensor rate 440 and the base rate 445. Therefore, this difference in individual sensor indicated rates exceeds the discrepancy threshold according to equation (1).

If the difference between any two sensor indicated rates during the same beat is greater than the discrepancy threshold, the microcontroller 60 determines, at decision step 325 of FIG. 3, if the difference between the last determined sensor indicated rates exceeded the discrepancy threshold. If not, then the detected discrepancy is the start of a new discrepancy incident, and the time and sensor indicated rates are recorded at step 330 to a designated block of memory 94.

If the last determined sensor indicated rates exceeded the discrepancy threshold is determined at decision step 325 to exceed the discrepancy threshold, then the detected discrepancy is considered to be an ongoing discrepancy incident. A duration counter or timer is then incremented at step 335 to track the duration of this discrepancy.

After recording the time and sensor indicated rates or incrementing a discrepancy duration counter, method 300 continues to the next cycle for determining sensor indicated rates at step 350. The sensor indicated rates are preferably re-determined at step 310 from the sensor signals obtained from physiologic sensor 108 on a periodic base, such as every second, or on a beat count basis, such as every beat.

When the difference between the sensor indicated rates does not exceed the discrepancy threshold, as determined at decision step 320, method 300 proceeds to decision step 340 to determine if the duration counter is greater than zero. If the duration counter is greater than zero, the current detection of sensor indicated rates that differ by less than the discrepancy threshold marks the end of a discrepancy incident. Therefore, at step 345, the value of the duration counter is stored as the discrepancy duration, and the duration counter is reset to zero. Method 300 then proceeds to step 350 where it continues to the next cycle of re-determining the sensor indicated rates at step 310.

If, however, the duration counter is not greater than zero at decision step 340, then method 300 proceeds directly to step 350 to continue monitoring for sensor indicated rate discrepancies during the next cycle of sensor indicated rate determinations. In this way, the time and duration of sensor indicated rate discrepancies and the sensor indicated rates are recorded in a sensor cross-check record located in memory 94.

The contents of the sensor cross-check record may be downloaded to an external device 102 for display and further analysis by a clinician. By observing an event record of sensor indicated rate discrepancies, the clinician may monitor abnormal patient conditions, such as Cheyne-Stokes respiration, or may recognize abnormal function of the sensors included in physiologic sensor 108 that requires replacement of the sensors or reprogramming of control parameters.

Furthermore, the clinician may use the sensor cross-check record exclusively as a monitoring tool without enabling the rate response capabilities of the device 10. This allows analysis of deviations in sensor indicated rates to be performed without affecting the stimulation rate in a potentially undesirable way.

In one embodiment, the time, duration, frequency, and discrepancy data detected during the operation of method 300 may be used by device 10 to automatically determine an appropriate rate response action. For example, if the minute ventilation sensor indicated rate is determined to be high and the activity sensor indicated rate is determined to be low and the time of the discrepancy is known to be night time, the incident is classified as a Cheyne-Stokes respiration episode and no stimulation rate adjustment is made. An increased heart rate is not needed because there is not a real increase in metabolic demand.

Conversely, if an activity sensor indicated rate is high and a minute ventilation sensor indicated rate is low and the duration of this discrepancy is continuous, the activity sensor is likely to be functioning inappropriately. Therefore, stimulation rate adjustments based on the activity sensor are disabled and a warning message is generated to be displayed to a clinician the next time data is downloaded to an external device 102.

However, short bouts of high activity and low minute ventilation sensor indicated rates, occurring at different times of the day, can be classified as relevant episodes of exertion. The stimulation rate can be appropriately adjusted according to the activity sensor indicated rate.

When the physiologic sensor 108 comprises multiple sensors, for example three sensors, if one sensor indicated rate deviates from the other two sensor indicated rates, the rate response may be based on the two sensor indicated rates that are in agreement.

For example, physiologic sensor 108 may include a minute ventilation sensor, a temperature sensor and an activity sensor. If the patient is sitting in a hot tub, the temperature sensor indicated rate will be high, but the activity sensor indicated rate will be low. The minute ventilation sensor indicated rate will also be relatively low. Therefore, the stimulation rate adjustment will be based on the two sensor indicated rates, activity and minute ventilation, which are in agreement and ignore the third.

As another example, if a patient is riding on a stationary bicycle, the minute ventilation sensor indicated rate will be high, the temperature sensor indicated rate will be high, but the activity sensor indicated rate may be relatively low. In this situation, the rate response will be based on the minute ventilation and temperature sensor indicated rates.

Figure 5:
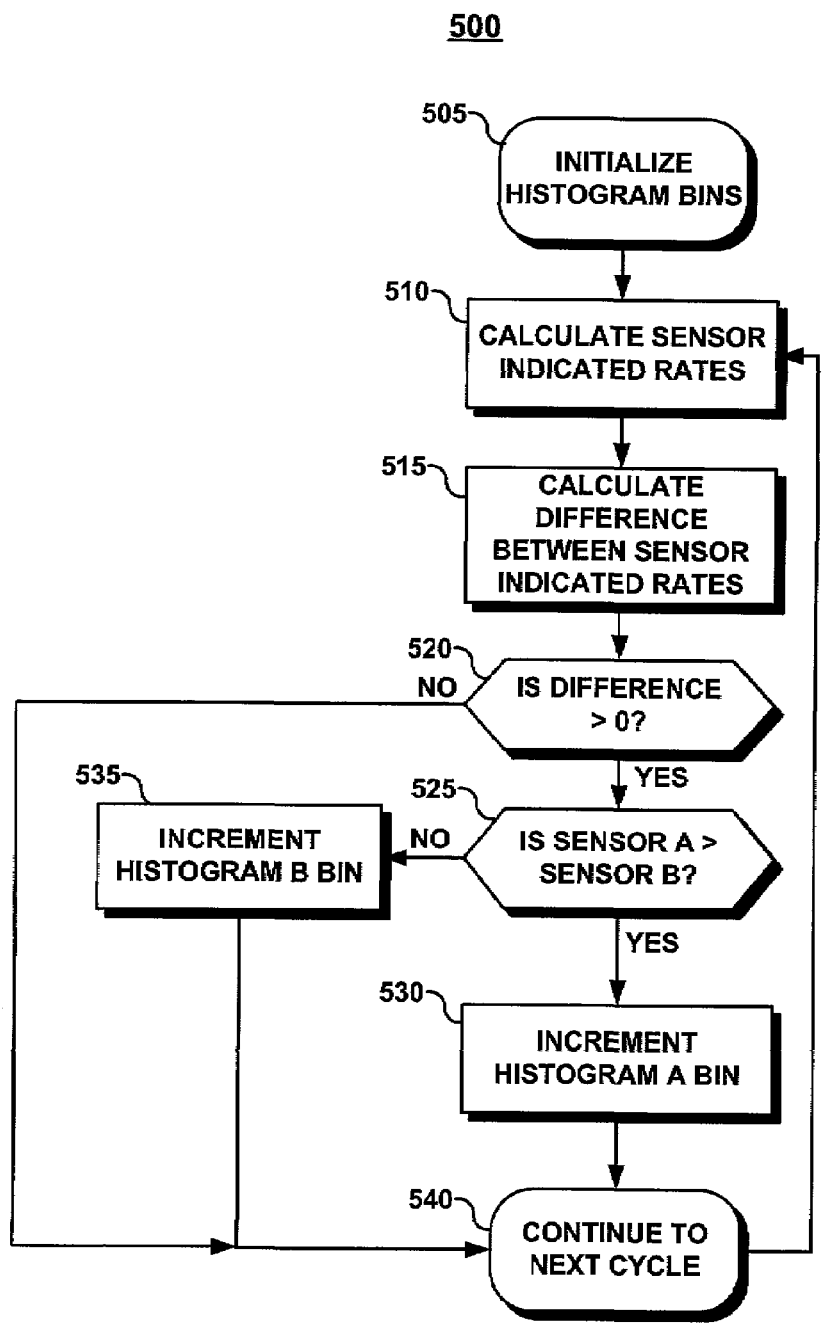
FIG. 5 is a flow chart that illustrates a method implemented by the stimulation device of FIGS. 1 and 2, for storing a histogram of sensor indicated rate differences.

FIG. 5 provides an overview of a method 500 included in another feature provided by the present invention, namely the provision of a sensor cross-check histogram. The sensor cross-check histogram may be implemented in the stimulation device 10 together with the sensor cross-check record, described above, or it may be implemented separately. If implemented together in the stimulation device 10, the user may choose to enable one or both features.

Method 500 begins at step 505 by initializing a set of histogram bins designated in the memory 94 for each sensor included in physiologic sensor 108 that will be used for determining a sensor indicated rate. Each set of histogram bins contains a bin assigned to a rate difference that will represent the difference between two sensor indicated rates.

Figure 6:
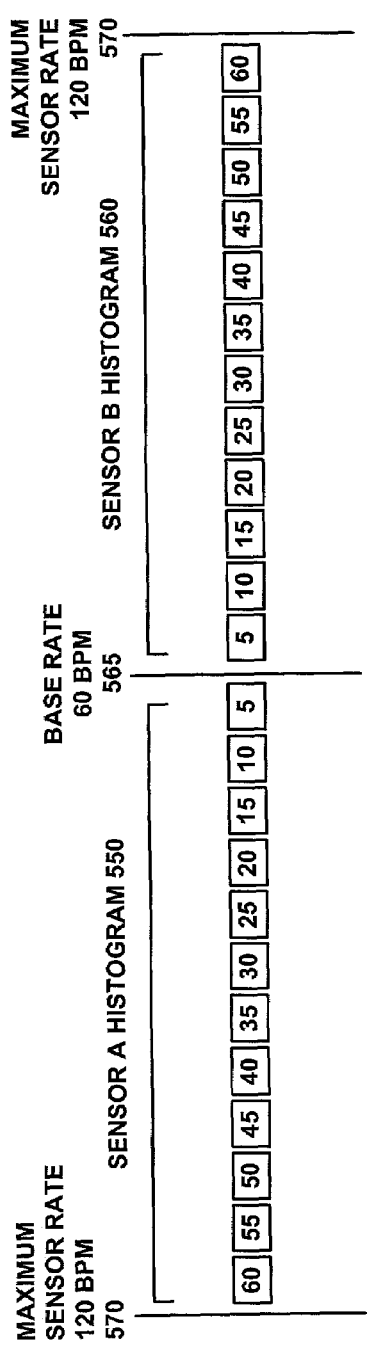
FIG. 6 is an illustration of one arrangement for assigning histogram bins to store a histogram of sensor indicated rates according to the method of FIG. 5.

FIG. 6 illustrates one arrangement of histogram bins in memory 94 that may be used when physiologic sensor 108 is equipped with two sensors referred to as sensor A and sensor B, that are used for determining sensor indicated rates. For this example, a base rate 565 is programmed to 60 beats per minute, and a maximum sensor rate 570 is programmed to 120 beats per minute.

Therefore, a maximum difference of 60 beats per minute is possible between two sensor indicated rates. Assuming the rate resolution of the stimulation device 10 is 5 beats per minute, twelve histogram bins are assigned to each of sensor A histogram 550 and sensor B histogram 560. In these histograms 550, 560, one bin is assigned for each 5 beats per minute of difference between the two sensor indicated rates.

At step 510 of method 500 (FIG. 5), microcontroller 60 calculates the sensor indicated rates from the signals received from physiologic sensor 108. At step 515, the difference between the sensor indicated rates is calculated. At decision step 520, microcontroller 60 determines if the difference between sensor indicated rates is greater than zero. If not, method 500 continues directly to step 540 where it will continue to the next cycle when sensor indicated rates are re-determined at step 510.

If a difference greater than zero is found at decision step 520, microcontroller 60 determines if the sensor indicated rate from sensor A is greater than the sensor indicated rate from sensor B at decision step 525. If the sensor indicated rate from sensor A is greater, a histogram bin assigned to sensor A is increased by one count at step 525. The sensor A histogram bin corresponding to the rate difference calculated at step 515 will be increased.

If, however, the sensor indicated rate from sensor A is not greater than the sensor indicated rate from sensor B at decision step 525, the histogram bin assigned to sensor B and corresponding to the rate difference calculated at step 515 is increased by one count at step 535. After the appropriate histogram bin is increased, the method 500 continues to step 540 where it will continue to the next cycle when the sensor indicated rates are re-determined at step 510.

The contents of the sensor cross-check histogram may be downloaded to an external device 102 to be displayed and analyzed further by a clinician. Histogram data may be displayed as a frequency distribution plot such as the sample results illustrated in FIGS. 7 through 10.

Figure 7:
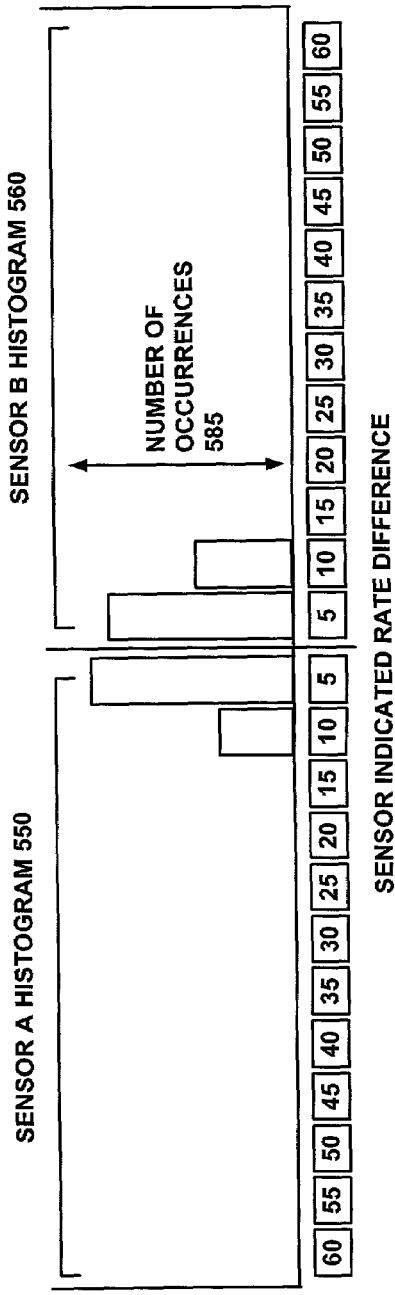
FIG. 7 is an illustration of example histogram results expected to occur during normal sensor function.

In FIG. 7, the number of occurrences 585 stored in sensor A histogram 550, in which sensor A indicates a greater rate than sensor B, is approximately equal to the number of occurrences of sensor B indicating a greater rate, as stored in sensor B histogram 560. These occurrences are distributed in an approximately normal distribution around a difference of zero. Differences of this magnitude are considered acceptable, therefore the operating parameters used in determining the sensor indicated rates are sufficient.

Figure 8:
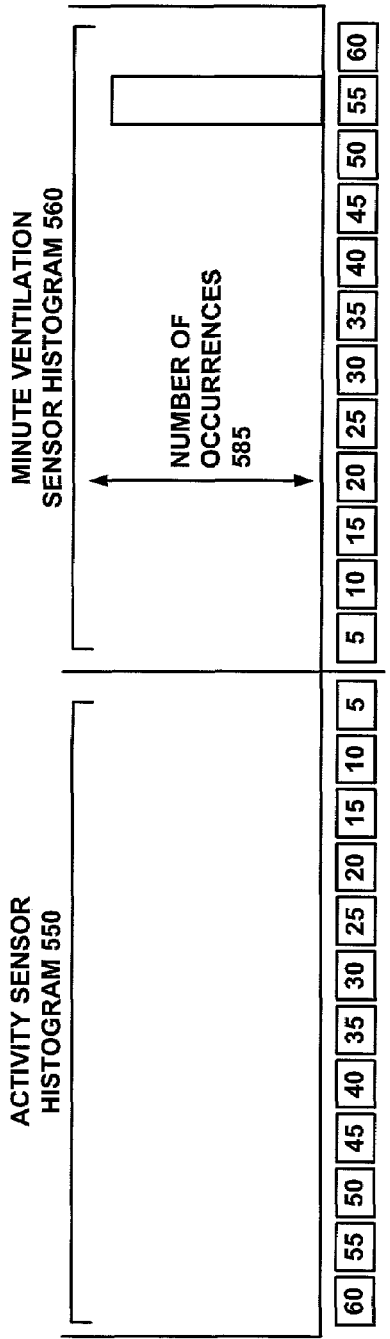
FIG. 8 is an illustration of example histogram results that may occur during an episode of abnormal respiration.

In FIG. 8, an uneven distribution of the sensor indicated rate differences is illustrated. In this case, sensor A is an activity sensor and sensor B is a minute ventilation sensor. A high frequency of minute ventilation sensor indicated rates that are considerably greater than the activity sensor indicated rate is displayed according to the contents of minute ventilation sensor histogram 560. This type of distribution suggests an abnormal respiration condition, for example hyperventilation, perhaps indicating episodes of Cheyne-Stokes respiration.

Figure 9:
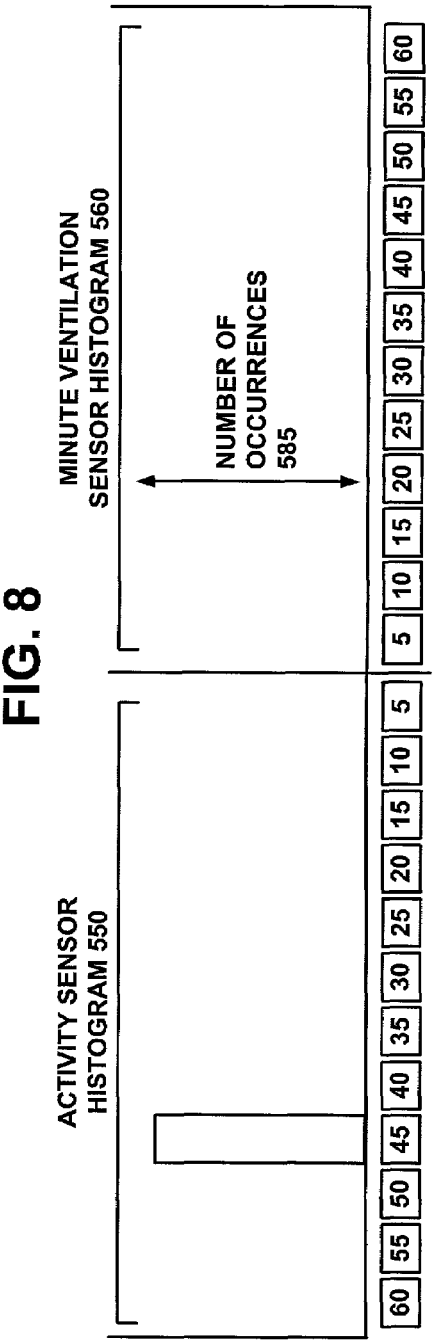
FIG. 9 is an illustration of example histogram results that may occur during abnormal sensor function.

In FIG. 9, an uneven distribution of the sensor indicated rate differences is shown in which the activity sensor frequently indicates sensor indicates rates much greater than the minute ventilation sensor as shown by the contents of activity sensor histogram 550 and minute ventilation sensor histogram 560. In this situation, the activity sensor may be functioning abnormally. Rate adjustments based on activity sensor indicated rates are preferably disabled until further analysis of the cause of this deviation from normal sensor indicated rate behavior is made.

Figure 10:
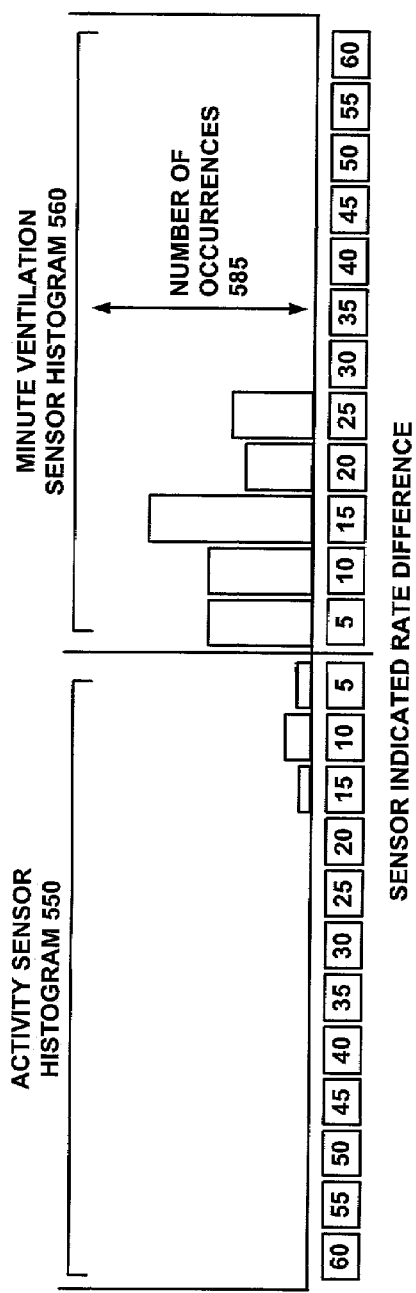
FIG. 10 is an illustration of example histogram results that may occur when operating parameters that control the determination of sensor indicated rates and rate response adjustments, are programmed sub-optimally.

In FIG. 10, an uneven distribution of the number of occurrences 585 of sensor indicated rate differences is shown in which the minute ventilation sensor histogram 550 has predominately higher indicated rates than the activity sensor histogram 560. In this situation the parameters used to determine the rate from the sensor signals may be programmed sub-optimally. An adjustment of these parameters, made automatically by the device 10 or manually by a physician, could correct this uneven distribution.

Figure 11:
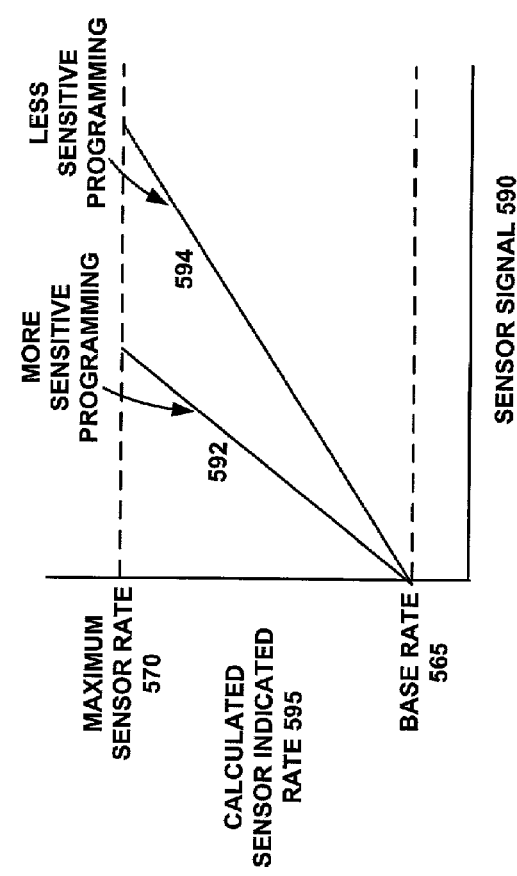
FIG. 11 is a graph illustrating the calculated sensor indicated rate as a function of the sensor signal when parameters controlling the sensor indicated rate calculation are programmed to be more sensitive or less sensitive to changes in the sensor signal.

As shown in FIG. 11, the sensor indicated rate 595 is calculated as a function of the sensor signal 590, in this example as a linear function. If the parameters used for calculating the sensor indicated rate are set such that the calculated sensor indicated rate is highly sensitive to changes in the sensor signal, resulting in relatively steep slope 592, the sensor indicated rates may be consistently higher than appropriate. If the parameters are programmed such that the calculated sensor indicated rate is less sensitive to changes in the sensor signal, resulting in a less steep slope 594, the sensor indicated rates may be consistently lower than appropriate.

The situation illustrated in FIG. 10, therefore, may represent programming that is too insensitive to changes in the activity sensor signal or too sensitive to changes in the minute ventilation sensor signal. The sensor cross-check histogram thus provides the clinician useful information in guiding the selection of parameters used for calculating sensor indicated rates.

Thus, a system and method for monitoring sensor indicated rate discrepancies has been described. A sensor cross check record provides a record of the time and duration of sensor indicated rate discrepancies such that the cause of such discrepancies, for example an abnormal patient condition, may be better understood and monitored. A sensor cross check histogram provides a record of the frequency and distribution of sensor indicated rate differences such that an abnormal patient condition, abnormal sensor function, or suboptimal sensor programming may be recognized. These features provide a physician with useful tools for monitoring a patient condition and for optimizing the rate responsive function of a stimulation device such that the goal of restoring normal sinus rhythm with varying levels of metabolic demand may be better achieved.

While detailed descriptions of specific embodiments of the present invention have been provided, it would be apparent to those reasonably skilled in the art that numerous variations of the methods described herein are possible in which the concepts of the present invention may readily be applied. The descriptions provided herein are for the sake of illustration and are not intended to be exclusive.

What is claimed is:

1. A method of monitoring sensor performance for use in a cardiac stimulation device, the method comprising:
   receiving sensor signals from a plurality of non-heart-rate sensors;
   processing the sensor signals to calculate sensor indicated rates for each sensor;
   calculating a difference between the sensor indicated rates; and
   storing the sensor indicated rates if the difference between the sensor indicated rates exceeds a discrepancy threshold.

2. The method according to claim 1, further comprising automatically adjusting rate response stimulation parameters based upon the stored sensor indicated rates.

3. The method according to claim 1, wherein if the sensor indicated rate discrepancy indicates an abnormal condition, further storing a time of occurrence of the sensor indicated rate discrepancy.

4. The method according to claim 1, further comprising storing a duration of the sensor indicated rate discrepancy.

5. The method according to claim 1, further comprising setting the discrepancy threshold as a programmable value.

6. The method according to claim 1, wherein receiving the sensor signals comprises receiving non-heart-rate signals from any one or more of:
   an activity sensor;
   a minute ventilation sensor;
   a pressure sensor;
   a temperature sensor;
   an oxygen sensor;
   a posture sensor; and
   a pH sensor.

7. The method according to claim 1, further comprising storing a most recent predetermined number of sensor indicated rate discrepancies.

8. A method of monitoring sensor performance for use in a cardiac stimulation device, the method comprising:
   receiving sensor signals from a plurality of sensors;
   processing the sensor signals to calculate sensor indicated rates for each sensor;
   calculating a difference between the sensor indicated rates;
   storing the sensor indicated rates if the difference between the sensor indicated rates exceeds a discrepancy threshold;
   increasing a value of a duration counter when both a current difference and a preceding difference between the sensor indicated rates exceed a discrepancy threshold; and
   setting the value of the duration counter as the duration of the sensor indicated rate discrepancy when the difference between the sensor indicated rates does not exceed a discrepancy threshold and the preceding difference between sensor indicated rates exceeded the discrepancy threshold.

9. A method of monitoring sensor performance for use in a cardiac stimulation device, the method comprising:
   receiving sensor signals from a plurality of sensors;
   processing the sensor signals to calculate sensor indicated rates for each sensor;
   calculating a difference between the sensor indicated rates;
   storing the sensor indicated rates if the difference between the sensor indicated rates exceeds a discrepancy threshold; and
   setting the discrepancy threshold as any of a predetermined percentage or a predefined percentage of a difference between a maximum sensor rate and a base rate.

10. A method of monitoring sensor performance for use in a cardiac stimulation device, the method comprising:
    receiving sensor signals from a plurality of sensors;
    processing the sensor signals to calculate sensor indicated rates for each sensor;
    calculating a difference between the sensor indicated rates;
    storing the sensor indicated rates if the difference between the sensor indicated rates exceeds a discrepancy threshold; and
    displaying stored discrepancy times, discrepancy durations, and sensor indicated rates.

11. The method according to claim 10, further comprising adjusting a rate response based on the stored discrepancy times, durations, and sensor indicated rates.

12. The method according to claim 10, further comprising selecting operating parameters that control the determination of a sensor indicated rate based on the stored discrepancy times, durations, and sensor indicated rates.

13. The method according to claim 10, further comprising monitoring a patients condition based on the stored discrepancy times, durations, and sensor indicated rates.

14. The method according to claim 10, further comprising detecting an abnormal sensor function based on the stored discrepancy times, durations, and sensor indicated rates.

15. A method of monitoring sensor performance for use in a cardiac stimulation device, the method comprising:
    receiving sensor signals from a plurality of sensors;
    processing the sensor signals to calculate sensor indicated rates for each sensor;
    calculating a difference between the sensor indicated rates;
    storing the sensor indicated rates if the difference between the sensor indicated rates exceeds a discrepancy threshold; and
    storing a histogram of sensor indicated rate differences by:
      assigning a set of histogram bins to first and second sensors, wherein each bin is assigned to a distinct rate difference; and
      increasing a value stored in a histogram bin assigned to the first sensor and to a rate difference, when the sensor indicated rate corresponding to the first sensor is greater than the sensor indicated rate corresponding to the second sensor.

16. The method according to claim 15, further comprising displaying a histogram of sensor indicated rate differences.

17. The method according to claim 15, further comprising monitoring a patients condition based on a histogram of the sensor indicated rate differences.

18. The method according to claim 15, further comprising detecting an abnormal sensor function based on the histogram of the sensor indicated rate differences.

19. The method according to claim 15, further comprising selecting operating parameters that control the determination of any of a sensor indicated rate or a rate response, based on the histogram of the sensor indicated rate differences.

20. A cardiac stimulation device for monitoring sensor performance, comprising:
    a plurality of non-heart-rate sensors that generate sensor signals;
    a memory that is configured to store sensor indicated rates; and
    a controller coupled to the memory and to the sensors, the controller being operative to receive sensor signals from the sensors and calculate sensor indicated rates based on the sensor signals, wherein the controller is operative to calculate a difference between the sensor indicated rates and store the sensor indicated rates in the memory if the difference between the sensor indicated rates exceeds a discrepancy threshold.

21. The cardiac stimulation device according to claim 20, wherein the controller further automatically adjusts rate response stimulation parameters based upon the stored sensor indicated rates.

22. The cardiac stimulation device according to claim 20, wherein if the difference between the sensor indicated rates indicates an abnormal condition, the controller is further operative to store a time of occurrence of the sensor indicated rate discrepancy in the memory.

23. The cardiac stimulation device according to claim 20, wherein a duration of the sensor indicated rate difference exceeding the threshold is stored in the memory.

24. The cardiac stimulation device according to claim 20, wherein the discrepancy threshold is a programmable value.

25. The cardiac stimulation device according to claim 20, wherein the sensor signals are received from any one or more of:
    an activity sensor;
    a minute ventilation sensor;
    a pressure sensor;
    a temperature sensor;
    an oxygen sensor;
    a posture sensor; and
    a pH sensor.

26. A cardiac stimulation device for monitoring sensor performance, comprising:
- a plurality of sensors that generate sensor signals;
- a memory that is configured to store sensor indicated rates;
- a controller coupled to the memory and to the sensors, the controller being operative to receive sensor signals from the sensors and calculate sensor indicated rates based on the sensor signals, wherein the controller is operative to calculate a difference between the sensor indicated rates and store the sensor indicated rates in the memory if the difference between the sensor indicated rates exceeds a discrepancy threshold, wherein the discrepancy threshold is any of a predetermined percentage or a predefined percentage of a difference between a maximum sensor rate and a base rate.

27. A cardiac stimulation device for monitoring sensor performance, comprising:
- a plurality of sensors that generate sensor signals;
- a memory that is configured to store sensor indicated rates;
- a controller coupled to the memory and to the sensors, the controller being operative to receive sensor signals from the sensors and calculate sensor indicated rates based on the sensor signals, wherein the controller is operative to calculate a difference between the sensor indicated rates and store the sensor indicated rates in the memory if the difference between the sensor indicated rates exceeds a discrepancy threshold; and
- a histogram that stores sensor indicated rate differences calculated by:
  - assigning a set of histogram bins to first and second sensors, wherein each bin is assigned to a distinct rate difference; and
  - increasing a value stored in a histogram bin assigned to the first sensor and to a rate difference, when the sensor indicated rate corresponding to the first sensor is greater than the sensor indicated rate corresponding to the second sensor.

28. The cardiac stimulation device according to claim 27, further comprising a display for displaying a histogram of sensor indicated rate differences.

29. A cardiac stimulation device for monitoring sensor performance, comprising:
- means for receiving non-heart-rate sensor signals from a plurality of sensors and for calculating sensor indicated rates for the sensor signals;
- means for calculating a difference between the sensor indicated rates;
- means for determining a sensor indicated rate discrepancy if the difference between the sensor indicated rates exceeds a discrepancy threshold; and
- means for storing the sensor indicated rates when a sensor indicated rate discrepancy is determined.

30. The cardiac stimulation device according to claim 29, further comprising means for automatically adjusting rate response stimulation parameters based upon the stored sensor indicated rates.

31. The cardiac stimulation device according to claim 29, wherein if the sensor indicated rate discrepancy indicates an abnormal condition, a time of occurrence and a duration of the sensor indicated rate discrepancy are stored in the storing means.

32. The cardiac stimulation device according to claim 29, wherein the discrepancy threshold is any of: a programmable value; a predefined percentage of a difference between a maximum sensor rate and a base rate; or predetermined percentage of a difference between a maximum sensor rate and a base rate.

33. The cardiac stimulation device according to claim 29, wherein the sensor signals are received from any one or more of:
- an activity sensor;
- a minute ventilation sensor;
- a pressure sensor;
- a temperature sensor;
- an oxygen sensor;
- a posture sensor; and
- a pH sensor.

34. The cardiac stimulation device according to claim 29, further comprising counting means for storing calculated sensor indicated rate differences.

* * * * *